United States Patent [19]

Pinkowski et al.

[11] Patent Number: 5,725,747
[45] Date of Patent: Mar. 10, 1998

[54] ELECTROCHEMICAL MEASUREMENT CELL

[75] Inventors: Alexander Pinkowski; Tiziana Chierchié, both of Rothenberg, Germany

[73] Assignee: ProMinent Dosiertechnik GmbH, Heidelberg, Germany

[21] Appl. No.: 636,960

[22] Filed: Apr. 24, 1996

[30] Foreign Application Priority Data

Apr. 26, 1995 [DE] Germany .................. 195 15 392.8

[51] Int. Cl.⁶ .................................................. G01N 27/26
[52] U.S. Cl. .................. 204/415; 204/412; 204/431; 204/432; 204/418; 422/82.02; 422/82.03
[58] Field of Search ................... 204/415, 412, 204/431, 432, 418; 422/82.03, 82.04

[56] References Cited

U.S. PATENT DOCUMENTS

| | | | |
|---|---|---|---|
| 3,575,836 | 4/1971 | Sternberg | 204/415 |
| 3,673,069 | 6/1972 | Niedrach et al. | 204/415 |
| 3,785,948 | 1/1974 | Hitchamn et al. | 204/195 P |
| 4,172,770 | 10/1979 | Semersky et al. | 204/412 |

FOREIGN PATENT DOCUMENTS

| | | |
|---|---|---|
| 0 050 035 A2 | 10/1981 | European Pat. Off. . |
| 0 289 199 A1 | 4/1988 | European Pat. Off. . |
| 34 05 431 | 11/1987 | Germany . |
| 34 22 233 | 12/1988 | Germany . |
| 48-90589 | 11/1973 | Japan . |
| WO 85/02465 | 6/1985 | WIPO . |

*Primary Examiner*—Bruce F. Bell
*Attorney, Agent, or Firm*—Darby & Darby

[57] ABSTRACT

It is an of this invention to provide an electrochemical measurement cell capable of measuring the concentration of gaseous and charged or neutral compounds in a liquid. Accordingly, the present invention consists in one aspect in an electrochemical measurement cell having a working and a counter electrode surrounded by an electrolyte space filled with an electrolyte with a high viscosity, wherein the electrolyte space is at least partly delimited by a hydrophilic membrane. It has been surprisingly discovered by the present invention that charged or neutral compounds in a liquid, as well as gases, can be determined by means of an electrochemical measurement cell having a hydrophilic membrane and an electrolyte with a high viscosity.

6 Claims, 1 Drawing Sheet

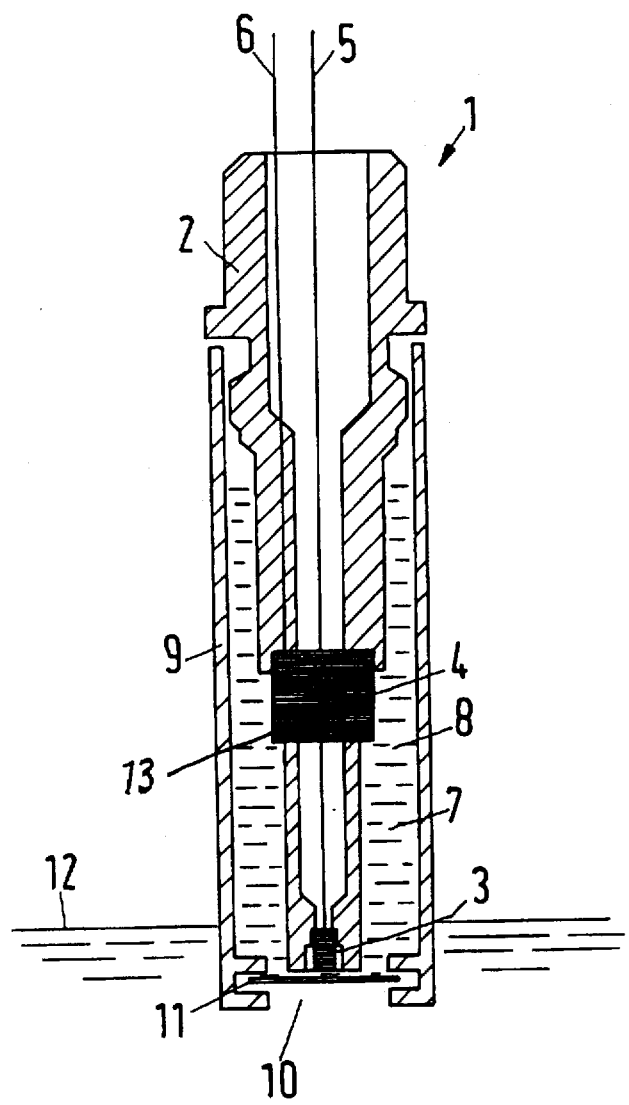

ELECTROCHEMICAL MEASUREMENT CELL

FIELD OF THE INVENTION

The present invention relates to an electrochemical measurement cell and particularly to an electrochemical measurement cell which is capable of measuring gases and charged and neutral compounds in a liquid.

BACKGROUND OF THE INVENTION

Numerous types of electrochemical measurement cells are presently in use. These cells generally consist of a working electrode, such as an ion-selective electrode, a redox potential electrode, an amperometric electrode, an enzyme electrode and a reference electrode. The purpose of the reference electrode in potentiometry is to provide a steady potential against which to measure the working electrode. The electrode generally contains an electrolyte which is separated from the sample by a membrane. If the sample to be measured is a liquid, hydrophobic membranes are often used in order to prevent leakage of the electrolyte, thereby preventing variation in measurements by the electrode due to changes in the sample electrolyte concentration and ionic strength.

The various elements which can be measured in a liquid using an electrode with a hydrophobic membrane is limited. In general, only gases can penetrate the hydrophobic membrane. Thus, neutral and charged compounds dissolved in a liquid cannot penetrate the hydrophobic membrane and therefore, go undetected. If a hydrophilic membrane is used, electrolyte may readily pass through the membrane and contaminate the sample.

SUMMARY OF THE INVENTION

It is an object of this invention to provide an electrochemical measurement cell capable of measuring the concentration of gaseous and charged or neutral compounds in a liquid. Accordingly, the present invention consists in one aspect in an electrochemical measurement cell having a working and a counter electrode surrounded by an electrolyte space filled with an electrolyte with a high viscosity, wherein the electrolyte space is at least partly delimited by a hydrophilic membrane. It has been surprisingly discovered by the present invention that charged or neutral compounds in a liquid, as well as gases, can be determined by means of an electrochemical measurement cell having a hydrophilic membrane and an electrolyte with a high viscosity.

BRIEF DESCRIPTION OF THE DRAWINGS

FIG. 1 is a schematic cross-section through an electrochemical measurement cell.

DETAILED DESCRIPTION OF THE INVENTION

The invention provides an electrochemical measurement cell capable of measuring the concentration of gaseous and charged or neutral compounds in a liquid.

The invention is described by means of an embodiment in conjunction with a drawing, FIG. 1.

An electrochemical measurement cell (1) having an electrode holder (2) a working electrode (3) and a counter electrode (4) serving at the same time as reference electrode (4). This configuration is referred to as a two-electrode arrangement. In another embodiment of this invention, in place of the counter and reference electrode (4), which are shown in FIG. 1 as one piece, the counter electrode (4) and the reference electrode (4) may also be separate from each other. This configuration is referred to as a three-electrode arrangement. The electrode holder further contains a connection (5) to the working electrode and a connection (6) to the reference electrode.

The electrodes (3), (4) are in contact with an electrolyte space (7) which is filled with an electrolyte (8).

The electrolyte space (7) is surrounded by a membrane cap (9) which exhibits an opening (10) which is closed off by a membrane (11). The concentration of gaseous and charged or neutral compounds is determined by dipping the opening (10) of measurement cell (1) a liquid (12).

Thus, the arrangement of the electrodes in the electrochemical measurement cell (1) of this invention can be configured with two electrodes as well as with three electrodes. The two-electrode arrangement contains a working electrode (3) and a counter electrode (4).

When a sample is measured during using a two-electrode arrangement, the determination of the unknown material is carried out more or less selectively by means of a potential which is applied between these two electrodes from the outside. With amperometric operation, during the analysis of the sample, a current flows which is proportional to the concentration of the substance being measured in the sample such as chlorine in water.

In special cases, the natural electromotive force which is present between the two electrodes and which derives from the positioning of the electrode materials that are being used in the so-called electrochemical displacement series is used as working potential.

In the three-electrode arrangement, the mechanism by which the concentration of the substance in the sample is being measured is similar. The three-electrode arrangement uses a reference electrode in addition to the working and counter electrodes. The working potential is applied between the working and reference electrodes using potentiostatic circuit, and the current is measured between the working and counter electrodes.

For both arrangements, it is necessary that the substance to be measured travels to the working electrode in order to create the desired measurement current by means of a reaction in the electrolyte space. In order to achieve this requirement, a membrane which is permeable to the substance to be measured and impermeable to the electrolyte is required. Traditionally, hydrophobic membranes were used to measure liquids in order to prevent the electrolyte from coming out of the measurement cell and to avoid penetration of the membrane by the liquid being measured.

The electrochemical measurement cell of this invention is capable of measuring gases and charged and neutral species in a liquid. By increasing the viscosity of the electrolyte, the loss of the electrolyte through the hydrophilic membrane and the penetration of the sample can be avoided or at least reduced to the extent that the proper functioning of the measurement cell is retained even over a long service lifetime.

When a hydrophobic membrane is used, the reaction products in the electrolyte space increase with time because they are not able to pass back through the hydrophobic membrane. In contrast, a hydrophilic membrane in conjunction with a high-viscosity electrolyte, the reaction products are able to go back through the membrane thereby reducing the retention of the reaction products in the electrolyte space. The service lifetime of the measurement cell is increased as a result.

The membrane used in the electrochemical measurement cell of this invention may be, for example, a polycarbonate or polyester film in which the pores are created by ions which are fired through the film with high energy, in conjunction with which the channels which result attain the desired pore size by means of high-precision chemical etching. Examples of membranes of a type are Cyclopore (Cyclopore, Belgium) or Nuclepore (Nuclepore, USA). The thicker the membrane and the smaller its pore size, the lower the viscosity of the electrolyte that can be selected.

In a preferred embodiment of this invention, the electrolyte is a liquid. A liquid electrolyte is free-flowing, thereby permitting the measurement cell to be easily refilled. As a result, proper functioning of the measurement cell can be extended practically as long as desired as far as the electrolyte is concerned. Of course, other factors can limit the service lifetime. Even the replacement of the electrolyte is facilitated. As long as the electrolyte is not solid but is rather a liquid, it can be removed from the electrolyte space by simply pouring it out. This is a particular advantage if the measurement cell is being used in an environment with a high level of contamination. Even with electrolytes with a high viscosity, replacement of the electrolyte is still possible without the electrode arrangement being exposed to the risk of damage as a result of a mechanical engagement in a solid electrolyte.

It is preferable that the viscosity of the electrolyte is adjusted depending upon the pore size and the thickness of the membrane in such a way that the leak rate of the cell remains under a predetermined value. The designation "high viscosity" is thus relative. The optimum viscosity is dependent on the individual measurement cell, and in particular, on the pore size and the thickness of the membrane. In the case of a thinner membrane, the viscosity is made higher than with a thicker one. With a smaller pore size, one can use a lower viscosity than when the pore size is larger. The standard of measure i r the viscosity, that is, the factor for assessing which viscosity is the correct one, is in accordance with the leak rate. The leak rate can be kept appropriately low by increasing the viscosity of the electrolyte.

It is preferred that the leak rate should not be greater than one half of the volume of the electrolyte space over a period of time in the range of from one to six months. Thus, during this period of time, no more that one half of the volume of the electrolyte space will pass through the membrane to the outside. This period of time derives from the preferred fields of application of the measurement cell.

One possible application, for example, is the measurement of chlorine in swimming pools. In that regard, the outdoor season is about six months long, and the pool director or the person who is responsible for the technical matters at the swimming pool prepares the measuring equipment before the start of the season in accordance with experience. The same holds true for indoor swimming pools. Thus, if the measurement cell with the electrolyte works satisfactorily within these six months because the electrolyte loss is kept within limits, then the latter is adequate. If necessary, one can plan on carrying out an interim maintenance procedure after about three months.

Another application, by way of example, is a measurement cell in the field of sewage clarification. In this application, the maintenance intervals are shorter, so that a maintenance procedure, that is, a changing or replenishing of the electrolyte will become necessary as a result of the slow but eventually complete outflow of the electrolyte as a result of the penetration of the liquid being measured into the electrolyte space, resulting in the dilution and contamination of in the electrolyte. The maintenance procedure is thus dependent on, among other things, the environment in which the measurement cell is working the level of contamination from the sample and the diameter of the particles of contamination.

In another preferred embodiment of this invention, the electrolyte contains a gelling agent. With the aid of such a gelling agent, an electrolyte that was previously of low viscosity becomes a gel-like electrolyte with a correspondingly higher viscosity with a practically no change of the electrolytic properties. Many times, this electrolyte gel can be poured into the electrolyte space while still in liquid form, with a low viscosity. The electrolyte gel will not harden until after it is in the electrolyte space. A gel of such a type will not become so solid that it cannot be removed from the electrolyte space. In this regard, it is preferable that the gelling agent is selected from the group of hydroxy ethylene celluloses. Even with the addition of electrolytes, the diluted solutions of the hydroxy ethylene celluloses are distinguished by their completely inert electrochemical behavior, so that the desired electrode reaction is not disturbed.

In order to further illustrate the present invention, the following example is provided. It should be understood that the invention is not limited to the specific example or the details described therein.

EXAMPLE I

This example describes a method of producing an electrolyte (8) with a high viscosity which can be used in the electrochemical measurement cell (1) of the present invention.

In order to create the higher viscosity, to the electrolyte (8) was added to a gelling agent which was chosen from a group of hydroxy ethylene celluloses. The gelling agent was not added to the electrolyte (8) until shortly before the electrolyte (8) was poured into the electrolyte space (7). Using this method, the electrolyte (8) still had a relatively low viscosity when it is poured. It subsequently gelled and formed a high-viscosity, free-flowing gel.

After gelling, it will not be possible to prevent the presence of a certain leak rate, which means that during the operation of the measurement cell (1), a certain portion of the electrolyte (8) will get through the membrane (11) into the sample (12). Because of the high viscosity of the electrolyte (8), however, this leak rate is so small that over a long period of time in the range of one to six months, at most a volume can escape that corresponds to one half of the volume of the electrolyte space (7). In this regard, the leak rate lies in the range of µl per day.

From 10 to 60 grams hydroxy ethylene cellulose (Merck 822068) was dissolved in one liter of electrolyte. The base electrolyte may consist of:

a. 0.01 to 3.5 molar potassium chloride (Merck 4936) solution when a silver/silver chloride reference electrode is being used, or b. 0.1 to 1 molar potassium iodide (Merck 5043) solution when a silver/silveriodide of reference electrode is being used.

The base electrolyte solutions of the specified molarity (concentration) were produced by dissolving the specified quantities of the particular salt in fully demineralized water.

What we claim is:

1. An electrochemical measurement cell comprising an electrode holder containing a working electrode and a counter electrode, said electrode holder surrounded by an electrolyte space containing an electrolyte, having a leak rate no greater than one-half of the volume of the electrolyte space for a period of one to six months, wherein the electrolyte comes into contact with the electrodes, wherein the electrolytic space is partly delimited by a hydrophilic membrane.

2. The electrochemical measurement cell of claim 1, wherein the electrolyte is not solid.

3. The electrochemical measurement cell of claim 1, wherein the electrode holder further contains a reference electrode.

4. The electrochemical measurement cell of claim 1, wherein the electrolyte contains a gelling agent.

5. The electrochemical measurement cell of claim 4, wherein the gelling agent is a hydroxy ethylene cellulose.

6. The electrochemical measurement cell of claim 1, wherein the hydrophilic membrane is a polycarbonate or polyester film.

* * * * *